United States Patent
Norizuki et al.

(10) Patent No.: US 9,518,031 B2
(45) Date of Patent: Dec. 13, 2016

(54) PHOTO-SENSITIVE RESIN COMPOSITION, CURED FILM, METHOD FOR FORMING A PIXEL, SOLID STATE IMAGE SENSOR, COLOR FILTER AND ULTRAVIOLET ABSORBER

(71) Applicant: FUJIFILM Corporation, Minato-ku, Tokyo (JP)

(72) Inventors: Yutaro Norizuki, Fujinomiya (JP); Yukie Watanabe, Fujinomiya (JP); Kazutaka Takahashi, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/867,796

(22) Filed: Sep. 28, 2015

(65) Prior Publication Data

US 2016/0016919 A1 Jan. 21, 2016

Related U.S. Application Data

(63) Continuation of application No. PCT/JP2014/058444, filed on Mar. 26, 2014.

(30) Foreign Application Priority Data

Mar. 29, 2013 (JP) ................... 2013-071374

(51) Int. Cl.

| G02B 5/20 | (2006.01) |
| G03F 7/004 | (2006.01) |
| C07D 263/14 | (2006.01) |
| G03F 7/031 | (2006.01) |
| G03F 7/00 | (2006.01) |
| G03F 7/16 | (2006.01) |
| G03F 7/20 | (2006.01) |
| G03F 7/32 | (2006.01) |
| G03F 7/40 | (2006.01) |

(52) U.S. Cl.
CPC ............. *C07D 263/14* (2013.01); *G02B 5/208* (2013.01); *G03F 7/004* (2013.01); *G03F 7/0007* (2013.01); *G03F 7/0045* (2013.01); *G03F 7/031* (2013.01); *G03F 7/16* (2013.01); *G03F 7/2002* (2013.01); *G03F 7/32* (2013.01); *G03F 7/40* (2013.01)

(58) Field of Classification Search
CPC .............. G03F 7/031; G03F 7/40; G03F 7/16; G03F 7/32; G03F 7/004; G03F 7/0045; G03F 7/2002; G03F 7/0007; G02B 5/208; G02B 5/223; G02F 1/133516; C07D 263/14
USPC ......... 430/7, 18, 270.1, 281.1, 330; 548/215
See application file for complete search history.

(56) References Cited

U.S. PATENT DOCUMENTS

| 8,908,293 B2 | 12/2014 | Maruyama et al. |
| 8,980,505 B2 | 3/2015 | Einaga |
| 2010/0323285 A1 | 12/2010 | Einaga |
| 2012/0257283 A1 | 10/2012 | Maruyama et al. |

FOREIGN PATENT DOCUMENTS

| JP | 2007-053153 A | 3/2007 |
| JP | 2009-067973 A | 4/2009 |
| JP | 2009-217221 A | 9/2009 |
| JP | 2011-073214 A | 4/2011 |
| JP | 2012-127096 A | 6/2011 |
| WO | WO 2012/086410 A1 * | 6/2012 |

OTHER PUBLICATIONS

Computer-generated translation of JP 2011-073214 (Apr. 2011).*
Computer-generated translation of JP 2009-067973 (Apr. 2009).*
International Preliminary Report on Patentability dated Oct. 8, 2015 from the International Bureau in counterpart International Application No. PCT/JP2014/058444.
International Search Report for PCT/JP2014/058444 dated Jun. 17, 2014 [PCT/ISA/210].
Written Opinion for PCT/JP2014/058444 dated Jun. 17, 2014 [PCT/ISA/237].
Office Action dated May 17, 2016, from the Japanese Patent Office in counterpart Japanese Application No. 2013-071374.
Office Action dated Oct. 10, 2016 from the Korean Patent Office in counterpart Korean Application No. 10-2015-7026482.

* cited by examiner

*Primary Examiner* — John A McPherson
(74) *Attorney, Agent, or Firm* — Sughrue Mion, PLLC

(57) ABSTRACT

Provided is a photo-sensitive composition capable of yielding pixels having a high translucency and a large refractive index, with a less amount of development residue in the process of formation. The photo-sensitive resin composition contains an ultraviolet absorber represented by Formula (I); a photo-polymerization initiator; and a polymerizable monomer: wherein each of $R^1$, $R^2$ and $R^3$ independently represents a hydrogen atom or an alkyl group having 1 to 10 carbon atoms; one of $R^4$ and $R^5$ represents an electron withdrawing group, and the other of $R^4$ and $R^5$ represents $-SO_2R^6$, $-CO_2R^6$, $-COR^6$, $-CN$ or $-CONR^6R^7$; each of $R^6$ and $R^7$ independently represents a hydrogen atom, alkyl group having 1 to 8 carbon atoms or aryl group.

Formula (I)

17 Claims, No Drawings

PHOTO-SENSITIVE RESIN COMPOSITION, CURED FILM, METHOD FOR FORMING A PIXEL, SOLID STATE IMAGE SENSOR, COLOR FILTER AND ULTRAVIOLET ABSORBER

CROSS-REFERENCE TO RELATED APPLICATIONS

This application is a Continuation of PCT International Application No. PCT/JP2014/058444 filed on Mar. 26, 2014, which claims priority under 35 U.S.C §119(a) to Japanese Patent Application No. 2013-071374 filed on Mar. 29, 2013. Each of the above application(s) is hereby expressly incorporated by reference, in its entirety, into the present application.

TECHNICAL FIELD

This invention relates to a photo-sensitive resin composition, and, a cured film, a solid state image sensor and a color filter using the same. This invention also relates to a method for forming a pixel using the photo-sensitive resin composition. This invention further relates to an ultraviolet absorber miscible to the photo-sensitive resin composition of this invention.

BACKGROUND ART

Color filters used for image sensors (CCD, CMOS, etc.) have been studied extensively (Patent Literature 1). Use of a photo-sensitive resin composition in order to form pixels of the color filter has also been studied (Patent Literature 2).

Patent Literatures 3 and 4 describe compounds having structures similar to those of the compounds used in this invention described later.

CITATION LIST

Patent Literature

[Patent Literature 1] JP-A-2007-53153
[Patent Literature 2] JP-A-2009-217221
[Patent Literature 3] JP-A-2011-73214
[Patent Literature 4] JP-A-2009-67973

SUMMARY OF THE INVENTION

Technical Problem

Now, the photo-sensitive resin composition, when intended to form the color filter of image sensor (also referred to as "solid state image sensor", hereinafter) or the color filter of liquid crystal display device, it is required that the obtainable pixels (cured film of the photo-sensitive resin composition) have a high translucency and a large refractive index, with only a small amount of development residue produced in the process of formation.

Meanwhile, compound VIII-7 described in paragraph [0097] of Patent Literature 3 (JP-A-2011-73214) has a structure similar to that of an ultraviolet absorber used in this invention. Compound VIII-7 has an alkylenoxy chain represented by $R^5$ in Formula (I). The alkylenoxy chain, however, makes the ultraviolet absorber itself less volatile, and less decomposable. This is because compound VIII-7 has an ether bond, and the moiety corresponded to $R^5$ can act as a polar group. Accordingly, the obtainable cured film will have a poor translucency, even with compound VIII-7 mixed therein. Regarding this point, difference in the effects will be discussed later in Examples of this patent application.

Patent Literature 4 (JP-A-2009-67973) describes mixing of an ultraviolet absorber to a polymer material. Patent Literature 4, however, aims to suppress bleed-out of the ultraviolet absorber, when mixed into the polymer material, over a long period of use. In other words, it aims to allow the ultraviolet absorber to stay long in the polymer material, even after the polymer material was made into film or the like. The ultraviolet absorber, thus remaining in the final product, will degrade the translucency.

As described above, any prior art has not successfully obtained a photo-sensitive resin composition which can provide a cured film capable of giving a high translucency and a large refractive index of the obtainable pixels (cured film of the photo-sensitive resin composition), and of producing only a small amount of development residue when the pixels are formed. It is therefore an object of this invention to solve these problems.

Solution to Problem

After studies under such situation, the present inventors found that the problems above may be solved by adding an ultraviolet absorber having a specific structure. More specifically, when the photo-sensitive resin composition is exposed with ultraviolet radiation at 365 nm to form the image, the resin composition added with the ultraviolet absorber will be more likely to absorb ultraviolet rays, enhanced in resolution, and reduced in development residue. While the ultraviolet absorber decomposes upon exposure, the ultraviolet absorber used in this invention decomposes to produce a highly translucent compound, thereby it is now possible to obtain a cured film with a large refractive index and a high translucency.

Specifically, the problems were solved by the solving means <1>, preferably by solving means <2> to <19> below.

<1> A photo-sensitive resin composition comprising:
an ultraviolet absorber represented by Formula (I);
a photo-polymerization initiator; and
a polymerizable monomer:

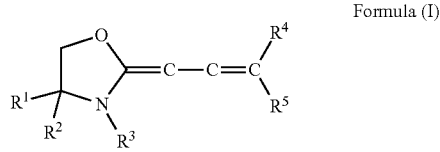

Formula (I)

wherein each of $R^1$, $R^2$ and $R^3$ independently represents a hydrogen atom or an alkyl group having 1 to 10 carbon atoms; one of $R^4$ and $R^5$ represents an electron withdrawing group, and the other of $R^4$ and $R^5$ represents $-SO_2R^6$, $-CO_2R^6$, $-COR^6$, $-CN$ or $-CONR^6R^7$; each of $R^6$ and $R^7$ independently represents a hydrogen atom, alkyl group having 1 to 8 carbon atoms or aryl group.

<2> The photo-sensitive resin composition of <1>, wherein Formula (I) is represented by Formula (II):

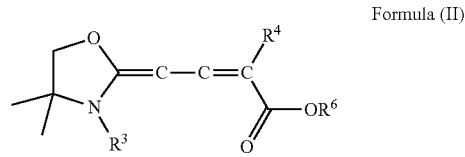

Formula (II)

wherein R³ represents a hydrogen atom or an alkyl group having 1 to 10 carbon atoms, and R⁴ represents —SO₂R⁶, —CO₂R⁶, —COR⁶, —CN or —CONR⁶R⁷; each of R⁶ and R⁷ independently represents a hydrogen atom, alkyl group having 1 to 8 carbon atoms or phenyl group.)

<3> The photo-sensitive resin composition of <1> or <2>, wherein R⁴ in Formula (I) or Formula (II) represents —SO₂R⁶ or —CO₂R⁶.

<4> The photo-sensitive resin composition of any one of <1> to <3>, which comprises the ultraviolet absorber represented by Formula (I) in an amount of 2 to 16% by mass, relative to a total solid content in the photo-sensitive resin composition.

<5> The photo-sensitive resin composition of any one of <1> to <4>, wherein the ultraviolet absorber represented by Formula (I) has a molecular weight of 150 to 850.

<6> The photo-sensitive resin composition of any one of <1>, <4> and <5>, wherein Formula (I) is represented by Formula (III):

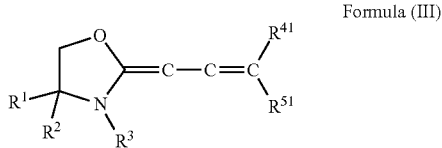

Formula (III)

wherein each of R¹, R² and R³ independently represents a hydrogen atom or alkyl group having 1 to 10 carbon atoms; each of R⁴¹ and R⁵¹ independently represents a secondary or tertiary alkyl ester group.

<7> The photo-sensitive resin composition of any one of <1> to <6>, wherein the ultraviolet absorber represented by Formula (I) is a compound represented by any of compounds (1) to (8) below:

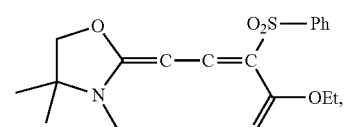
1

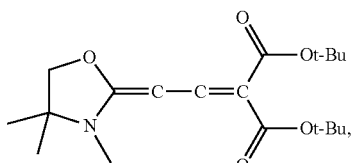
2

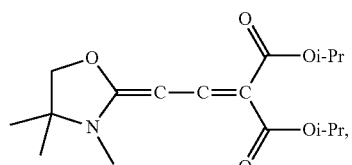
3

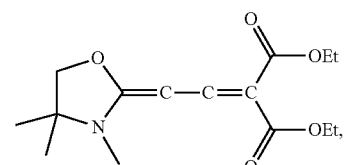
4

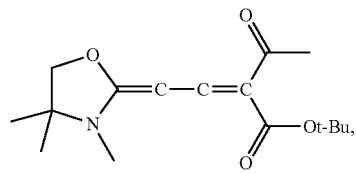
5

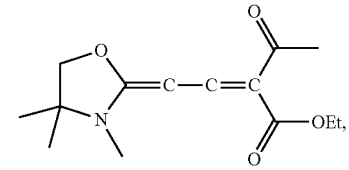
6

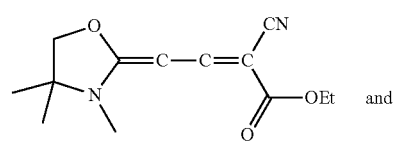
7
and

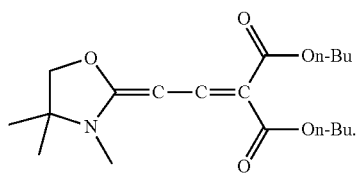
8

<8> The photo-sensitive resin composition of any one of <1> to <7>, containing an oxime compound as the photo-polymerization initiator.

<9> The photo-sensitive resin composition of any one of <1> to <8>, further comprising a particle having a refractive index at 500 nm of 1.80 to 2.80.

<10> The photo-sensitive resin composition of <9>, wherein the particle is composed of titanium dioxide and/or zirconium oxide.

<11> The photo-sensitive resin composition of any one of <1> to <10>, further comprising a dye and/or a pigment.

<12> The photo-sensitive resin composition of any one of <1> to <11>, further comprising an alkali-soluble resin.

<13> The photo-sensitive resin composition of any one of <1> to <12>, intended to be used in formation of pixels of a solid state image sensor or a liquid crystal display device.

<14> A cured film obtained by curing the photo-sensitive resin composition described in any one of <1> to <13>.

<15> The cured film of <14>, which comprises the ultraviolet absorber represented by Formula (I) in an amount of 0.01% by mass or less relative to the cured film.

<16> A method for forming a pixel, the method comprising:
coating the photo-sensitive resin composition described in any one of <1> to <13>; and
photo-irradiating the thus-formed layer with at least ultraviolet radiation through a photomask, and then developing the layer to form a pattern; and
post-baking the thus formed pattern.

<17> A color filter comprising the pixel formed by the method for forming a pixel described in <16>.

<18> A solid state image sensor comprising the color filter described in <17>.

<19> A liquid crystal display device comprising the color filter described in <17>.

<20> An ultraviolet absorber represented by Formula (III):

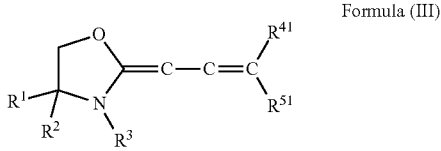

Formula (III)

wherein each of $R^1$, $R^2$ and $R^3$ independently represents a hydrogen atom or alkyl group having 1 to 10 carbon atoms; each of $R^{41}$ and $R^{51}$ independently represents a secondary or tertiary alkyl ester group.

Advantageous Effects of Invention

It now became possible to provide a photo-sensitive composition capable of yielding pixels (cured film of the photo-sensitive resin composition) having a high translucency and a large refractive index, with a less amount of development residue in the process of formation.

DESCRIPTION OF EMBODIMENTS

The present invention will be detailed below. Note, while the explanation on the constituents described below will occasionally be made based on representative embodiments of this invention, this invention by no means limited to these embodiments. Note in this specification that the wording "to" with preceding and succeeding numerals is used for indicating a numerical range with the lower and upper limits thereof respectively given by these numerals.

In this specification, "(meth)acrylate" means acrylate and methacrylate, "(meth)acryl" means acryl and methacryl, "(meth)acryloyl" means acryloyl and methacryloyl. In this specification, the term "monomer" and "monomer" is synonymous. The monomer in the present invention is discriminated from oligomer and polymer, and means any compound having a weight-average molecular weight of 2,000 or smaller. In this specification, the polymerizable compound means any compound having a polymerizable functional group, and may be a monomer or polymer. The polymerizable functional group means any group participating a polymerization reaction.

In the nomenclature of group (atomic group) in this specification, any expression without indication of "substituted" or "unsubstituted" includes both cases having no substituent and having a substituent. For example, "alkyl group" includes not only an alkyl group having no substituent (unsubstituted alkyl group) but also an alkyl group having a substituent (substituted alkyl group).

The photo-sensitive resin composition of this invention, the color filter and the method of manufacturing the same, the solid state image sensor and the liquid crystal display device will be detailed below. Note, while the explanation on the constituents described below will occasionally be made based on representative embodiments of this invention, this invention by no means limited to these embodiments.

The photo-sensitive resin composition of this invention (may simply be referred to as "composition of this invention", hereinafter) characteristically contains an ultraviolet absorber represented by Formula (I) above, a photo-polymerization initiator, and a polymerizable monomer. With such configuration, obtainable is the photo-sensitive resin composition suitable for forming pixels of the color filter. The pixels may be colored in red, green, blue and so forth, and may even be clear (white pixels) for which the present invention is particularly suitable.

The composition of this invention will be detailed below.
<Ultraviolet Absorber Represented by Formula (I)>

In this invention, an ultraviolet absorber represented by the Formula (I) is mixed. The ultraviolet absorber represented by Formula (I) is preferably a compound having an absorption maximum in the range from 250 nm to 400 nm. By mixing such component, it now becomes possible to obtain a cured film producing only a small amount of development residue when developed, having a large refractive index, and having a high translucency.

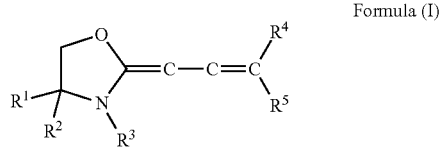

Formula (I)

(In Formula (I), each of $R^1$, $R^2$ and $R^3$ independently represents a hydrogen atom or an alkyl group having 1 to 10 carbon atoms. One of $R^4$ and $R^5$ represents an electron withdrawing group, and the other of $R^4$ and $R^5$ represents $-SO_2R^6$, $-CO_2R^6$, $-COR^6$, $-CN$ or $-CONR^6R^7$. Each of $R^6$ and $R^7$ independently represents a hydrogen atom, alkyl group having 1 to 8 carbon atoms, or aryl group.)

The alkyl group in Formula (I) is an unsubstituted alkyl group, and the aryl group is an unsubstituted aryl group.

Each of $R^1$, $R^2$ and $R^3$ independently represents a hydrogen atom or alkyl group having 1 to 10 carbon atoms, and preferably an alkyl group having 1 to 10 carbon atoms. While the alkyl group may be any of straight-chain, branched, and cyclic alkyl groups, it is preferably straight-chain or branched alkyl group, and more preferably straight-chain alkyl group. More specifically, it is preferable that each of $R^1$ and $R^2$ independently represents an alkyl group having 1 to 4 carbon atoms, more preferably a methyl group, ethyl group, isopropyl group, butyl group, sec-butyl group or tert-butyl group, and even more preferably a methyl group.

One of $R^4$ and $R^5$ represents an electron withdrawing group, and the other represents $-SO_2R^6$, $-CO_2R^6$, $-COR^6$, $-CN$ or $-CONR^6R^7$.

The electron withdrawing group is preferably $-SO_2NR^6R^7$, $-NO_2$, $-CN$, $-SO_2R^6$, $-CO_2R^6$, $-COR^6$, $-CN$ or $-CONR^6R^7$, more preferably $-CN$, $-SO_2R^6$, $-CO_2R^6$, $-COR^6$, $-CN$ or $-CONR^6R^7$, even more preferably $-SO_2R^6$ or $-CO_2R^6$, and particularly $-CO_2R^6$.

The other one of $R^4$ and $R^5$ represents $-SO_2R^6$, $-CO_2R^6$, $-COR^6$, $-CN$ or $-CONR^6R^7$, more preferably $-SO_2R^6$ or $-CO_2R^6$, and particularly $-CO_2R^6$.

Each of $R^6$ and $R^7$ independently represents a hydrogen atom, alkyl group having 1 to 8 carbon atoms or aryl group, preferably represents a hydrogen atom, alkyl group having 1 to 8 carbon atoms or phenyl group, and even more preferably a hydrogen atom, alkyl group having 1 to 4 carbon atoms or phenyl group. While the alkyl group may be any of straight-chain, branched and cyclic alkyl groups, it is preferably straight-chain or branched alkyl group, and more preferably straight-chain alkyl group. More specifically, the alkyl group having 1 to 8 carbon atoms is preferably a methyl group, ethyl group, isopropyl group, butyl group, sec-butyl group, tert-butyl group, pentyl group, tert-pentyl group, hexyl group, octyl group, 2-ethylhexyl group, or tert-octyl group, and more preferably methyl group, ethyl group, isopropyl group, butyl group, sec-butyl group, or tert-butyl group.

From the viewpoint of further improving the transmittance after post-baking, each of $R^6$ and $R^7$ preferably represents a secondary or tertiary alkyl group having 3 or 4 carbon atoms (for example, isopropyl group, sec-butyl group, tert-butyl group).

Formula (I) is preferably represented by Formula (II) below.

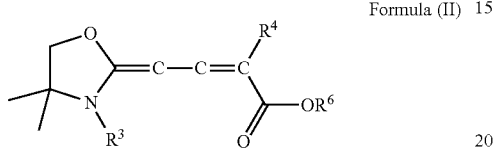

Formula (II)

(In Formula (II) $R^3$ represents a hydrogen atom or alkyl group having 1 to 10 carbon atoms, and $R^4$ represents —$SO_2R^6$, —$CO_2R^6$, —$COR^6$, —CN or —$CONR^6R^7$. Each of $R^6$ and $R^7$ independently represents a hydrogen atom, alkyl group having 1 to 8 carbon atoms, or phenyl group.)

$R^3$, $R^4$, $R^6$ and $R^7$ in Formula (II) are respectively synonymous to $R^3$, $R^4$, $R^6$ and $R^7$ in Formula (I), while defined by the same preferable ranges. A particularly preferable embodiment is exemplified by an embodiment where $R^4$ in Formula (II) represents —$SO_2R^6$ or —$CO_2R^6$.

Formula (I) is also preferably represented by Formula (III) below. The ultraviolet absorber represented by Formula (III) is also preferably used as the ultraviolet absorber for applications other than the photo-sensitive resin composition.

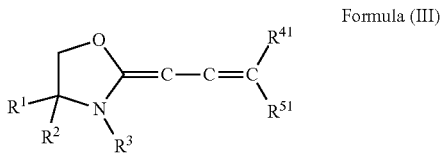

Formula (III)

(In Formula (III), each of $R^1$, $R^2$ and $R^3$ independently represents a hydrogen atom or alkyl group having 1 to 10 carbon atoms. Each of $R^{41}$ and $R^{51}$ independently represents a secondary or tertiary alkyl ester group.)

$R^3$, $R^4$, $R^6$ and $R^7$ in Formula (III) are respectively synonymous to $R^3$, $R^4$, $R^6$ and $R^7$ in Formula (I), while defined by the same preferable ranges.

The ultraviolet absorber represented by Formula (I) preferably has a molecular weight of 150 to 850, more preferably 150 to 650, and even more preferably 150 to 450. Within these ranges, the effect of this invention may be demonstrated in a more efficient manner.

Specific examples of the ultraviolet absorber represented by Formula (I) will be listed below. Note that this invention is not limited to these examples. In Table below, Me denotes methyl group, Ph denotes phenyl group, Et denotes ethyl group, Bu denotes butyl group, and Pr denotes propyl group. In this invention, Compounds 1 to 8 below are particularly preferable.

TABLE 1

| Compound | $R^1$ | $R^2$ | $R^3$ | $R^4$ | $R^5$ |
|---|---|---|---|---|---|
| 1 | Me | Me | Me | $SO_2Ph$ | $CO_2Et$ |
| 2 | Me | Me | Me | $CO_2t$-Bu | $CO_2t$-Bu |
| 3 | Me | Me | Me | $CO_2i$-Pr | $CO_2i$-Pr |
| 4 | Me | Me | Me | $CO_2Et$ | $CO_2Et$ |
| 5 | Me | Me | Me | COMe | $CO_2t$-Bu |
| 6 | Me | Me | Me | COMe | $CO_2Et$ |
| 7 | Me | Me | Me | CN | $CO_2Et$ |
| 8 | Me | Me | Me | $CO_2n$-Bu | $CO_2n$-Bu |
| 9 | Me | Me | Me | CN | CONHn-Bu |
| 10 | Me | Me | Et | $SO_2Ph$ | CN |
| 11 | Me | Me | Et | $SO_2Et$ | COPh |
| 12 | Me | Me | Et | $SO_2Ph$ | CONHEt |
| 13 | Me | Me | Et | $SO_2Ph$ | $SO_2Ph$ |
| 14 | Me | Me | i-Pr | $CO_2Me$ | CONHn-Et |
| 15 | Me | Me | H | CN | CN |
| 16 | Me | Me | H | CN | COt-Bu |
| 17 | H | H | Et | COEt | COEt |
| 18 | Et | H | Me | COMe | $CONHC_8H_{17}$ |
| 19 | H | H | H | CONHPh | CONHPh |
| 20 | i-Pr | H | Me | $SO_2C_8H_{17}$ | $CO_2Ph$ |
| 21 | H | H | t-Bu | $CO_2Ph$ | $CO_2tPh$ |
| 22 | H | H | H | $COC_8H_{17}$ | $CO_2Me$ |
| 23 | H | H | $C_{10}H_{21}$ | CN | $CONMe_2$ |
| 24 | Et | H | H | $SO_2Me$ | $CONPh_2$ |
| 25 | Me | H | $C_8H_{17}$ | $CO_2Et$ | $CO_2Et$ |
| 26 | i-Pr | H | Me | COMe | $CO_2Et$ |
| 27 | $C_{10}H_{21}$ | H | H | CN | $CO_2Et$ |
| 28 | Me | Me | H | COMe | $COC_8H_{17}$ |

The amount of mixing of the ultraviolet absorber represented by Formula (I), relative to the total solid content in the photo-sensitive resin composition of this invention, is preferably 0.01% by mass to 30% by mass, more preferably 0.1% by mass to 20% by mass, even more preferably 2 to 16% by mass, and yet more preferably 2 to 10% by mass. With the content of the ultraviolet absorber represented by Formula (I) controlled to 0.01% by mass or more, the composition will have a good light shielding ability in the process of exposure, which is advantageous in terms of preventing thickening of pattern width due to excessive progress of polymerization, more easily obtaining a target line width, and suppressing the peripheral residue (development residue). Meanwhile, with the content controlled to 30% by mass or less, the light shielding ability in the process of exposure will be not excessively strong, and thereby the polymerization can proceed more suitably. In particular in this invention, with the amount of addition of the ultraviolet absorber represented by Formula (I) controlled to 2 to 16% by mass relative to the total solid content, the effect of this invention will be demonstrated in a more efficient manner.

In this invention, only one species of the ultraviolet absorber represented by Formula (I) may be used, or two or more species may be used. When two or more species are used, the total content preferably satisfies the amount of mixing described above.

The ultraviolet absorber represented by Formula (I) may be synthesized referring to the methods described in JP-B-S44-29620, JP-A-53-128333, JP-A-S61-169831, JP-A-S63-53543, JP-A-S63-53544, JP-A-S63-56651, JP-A-2009-96973, and references cited in these patent literatures.

While the photo-sensitive resin composition of this invention may contain an ultraviolet absorber other than those represented by Formula (I) above, it is preferable that the composition contains substantially no ultraviolet absorber other than those represented by Formula (I). The phrase of "contains substantially no ultraviolet absorber" now means that the content is, for example, 10% by mass or less relative to the amount of mixing of the ultraviolet absorber represented by Formula (I), and more preferably 1% by mass or less.

<Photo-Polymerization Initiator>

The photo-sensitive resin composition of this invention contains at least one species of photo-polymerization initiator. The photo-polymerization initiator is exemplified by oxime compound, organohalogen compound, oxadiazole compound, carbonyl compound, ketal compound, benzoin compound, acridine compound, organic peroxy compound, azo compound, coumarin compound, azide compound, metallocene compound, hexaarylbiimidazole compound, organoborate compound, disulfone compound, onium salt compound, and acylphosphine (oxide) compound. Oxime compound is preferable by virtue of its large light absorptivity and capability of enhancing sensitivity.

The oxime compound may be referred to the description of compounds represented by Formula (OX-1), (OX-2) or (OX-3), in paragraph [0513] of JP-A-2012-208494 (paragraph [0632] in corresponded U.S. Patent Application No. 2012/235099) and succeeding paragraphs, the contents of which are incorporated into this specification.

Specific examples of the oxime compound include, but not limited to, 2-(O-benzoyloxime)-1-[4-(phenylthio)phenyl]-1,2-butanedione,
2-(O-benzoyloxime)-1-[4-(phenylthio)phenyl]-1,2-pentanedione,
2-(O-benzoyloxime)-1-[4-(phenylthio)phenyl]-1,2-hexanedione,
2-(O-benzoyloxime)-1-[4-(phenylthio)phenyl]-1,2-heptanedione,
2-(O-benzoyloxime)-1-[4-(phenylthio)phenyl]-1,2-octanedione,
2-(O-benzoyloxime)-1-[4-(methylphenylthio)phenyl]-1,2-butanedione,
2-(O-benzoyloxime)-1-[4-(ethylphenylthio)phenyl]-1,2-butanedione,
2-(O-benzoyloxime)-1-[4-(butylphenylthio)phenyl]-1,2-butanedione,
1-(O-acetyloxime)-1-[9-ethyl-6-(2-methylbenzoyl)-9H-carbazole-3-yl]ethanone,
1-(O-acetyloxime)-1-[9-methyl-6-(2-methylbenzoyl)-9H-carbazole-3-yl]ethanone,
1-(O-acetyloxime)-1-[9-propyl-6-(2-methylbenzoyl)-9H-carbazole-3-yl]ethanone,
1-(O-acetyloxime)-1-[9-ethyl-6-(2-ethylbenzoyl)-9H-carbazole-3-yl]ethanone, and
1-(O-acetyloxime)-1-[9-ethyl-6-(2-butylbenzoyl)-9H-carbazole-3-yl]ethanone.

Particularly preferable examples of the oxime compound include 2-(O-benzoyloxime)-1-[4-(phenylthio)phenyl]-1,2-octanedione, and 1-(O-acetyloxime)-1-[9-ethyl-6-(2-methylbenzoyl)-9H-carbazole-3-yl]ethanone. Among commercially available products, preferable examples include Irgacure OXE 01 (1,2-octanedione,1-[4-(phenylthio)-,2-(O-benzoyloxime)]) and Irgacure OXE 02 (ethanone,1-[9-ethyl-6-(2-methylbenzoyl)-9H-carbazole-3-yl]-,1-(O-acetyloxime)) from BASF; and TR-PBG-304 (from Changzhou Tronly New Electronic Materials Co., Ltd.).

The organohalogen compound is specifically exemplified by those described in Wakabayashi et al., Bull. Chem. Soc. Japan, 42, 2924 (1969), U.S. Pat. No. 3,905,815, JP-B-S46-4605, JP-A-S48-36281, JP-A-S55-32070, JP-A-S60-239736, JP-A-S61-169835, JP-A-S61-169837, JP-A-S62-58241, JP-A-S62-212401, JP-A-S63-70243, JP-A-S63-298339, and M. P. Hutt, *Journal of Heterocyclic Chemistry*, 1(No. 3), (1970), the contents of which are incorporated into this specification. In particular, oxazole compound substituted by a trihalomethyl group, and s-triazine compound are exemplified.

The s-triazine compound is more preferably exemplified by s-triazine derivatives, having at least one mono-, di- or tri-halogenated methyl groups bound to the s-triazine ring. This is exemplified by halomethyltriazine compound, and further by the compounds described in paragraph [0132] of JP-A-2012-255148, the contents of which are incorporated into this specification.

The oxadiazole compound is exemplified by the compounds described in paragraph [0133] of JP-A-2012-255148, the contents of which are incorporated into this specification.

The carbonyl compound is exemplified by the compounds described in paragraph [0134] of JP-A-2012-255148, the contents of which are incorporated into this specification.

The ketal compound is exemplified by benzyl methyl ketal and benzyl-β-methoxyethylethyl acetal.

The benzoin compound is exemplified by the compounds described in paragraph [0136] of JP-A-2012-255148, the contents of which are incorporated into this specification.

The acridine compound is exemplified by 9-phenylacridine and 1,7-bis(9-acridinyl)heptane.

The organic peroxy compound is exemplified by the compounds described in paragraph [0138] of JP-A-2012-255148, the contents of which' are incorporated into this specification.

The azo compound is exemplified by the azo compounds described in JP-A-H08-108621.

The coumarin compound is exemplified by
3-methyl-5-amino-((s-triazine-2-yl)amino)-3-phenylcoumarin,
3-chloro-5-diethylamino-((s-triazine-2-yl)amino)-3-phenylcoumarin, and
3-butyl-5-dimethylamino-((s-triazine-2-yl)amino)-3-phenylcoumarin.

The azide compound is exemplified by the organic azide compounds described in U.S. Pat. No. 2,848,328, U.S. Pat. No. 2,852,379 and U.S. Pat. No. 2,940,853, and 2,6-bis(4-azidobenzylidene)-4-ethylcyclohexanone (BAC-E).

The metallocene compound is exemplified by the compounds described in paragraph [0142] of JP-A-2012-255148, the contents of which are incorporated into this specification.

The hexaarylbiimidazole compound is exemplified by the compounds described in paragraph [0143] of JP-A-2012-255148, the contents of which are incorporated into this specification.

The organoborate compound is specifically exemplified by organoborates described in patent literatures including JP-A-S62-143044, JP-A-S62-150242, JP-A-H09-188685, JP-A-H09-188686, JP-A-H09-188710, JP-A-2000-131837, JP-A-2002-107916, Japanese Patent No. 2764769 and Japanese Patent Application No. 2000-310808, and in Martin Kunz, "*RadTech '98 Proceeding, Apr.* 19-22, 1998, *Chicago*"; organic boron sulfonium complexes or organic boron oxosulfonium complexes described in JP-A-H06-157623, JP-A-H06-175564 and JP-A-H06-175561; organic boron iodonium complexes described in JP-A-H06-175554 and JP-A-H06-175553; organic boron phosphonium complex described in JP-A-H09-188710; and organic boron-transition metal coordination complexes described in JP-A-H06-348011, JP-A-H07-128785, JP-A-H07-140589, JP-A-H07-306527 and JP-A-H07-292014.

The disulfone compound is exemplified by the compounds described in JP-A-S61-166544 and JP-A-2002-328465 (Japanese Patent Application No. 2001-132318).

The onium salt compound is exemplified by diazonium salts described in S. I. Schlesinger, *Photogr. Sci. Eng.*, 18, 387 (1974) and T. S. Bal et al., *Polymer*, 21, 423(1980); ammonium salts described in U.S. Pat. No. 4,069,055 and JP-A-H04-365049; phosphonium salts described in U.S. Pat. No. 4,069,055 and U.S. Pat. No. 4,069,056; and iodonium salts described in European Patent No. 104,143, U.S. Pat. No. 339,049, U.S. Pat. No. 410,201, JP-A-H02-150848 and JP-A-H02-296514.

The iodonium salt is a diaryl iodonium salt, and, from the viewpoint of safety, preferably substituted by two or more electron donating groups such as alkyl group, alkoxy group, or aryloxy group.

Preferable forms of the sulfonium salt are exemplified by iodonium salts, in which one substituent of triaryl sulfonium salt has a coumarin or anthraquinone structure, and showing absorption at 300 nm or longer.

The sulfonium salt is exemplified by those described in European Patent No. 370,693, ditto 390,214, ditto 233,567, ditto 297,443, ditto 297,442, U.S. Pat. No. 4,933,377, U.S. Pat. No. 161,811, U.S. Pat. No. 410,201, U.S. Pat. No. 339,049, U.S. Pat. No. 4,760,013, U.S. Pat. No. 4,734,444, U.S. Pat. No. 2,833,827, German Patent No. 2,904,626, ditto 3,604,580, and ditto 3,604,581, which are preferably substituted by an electron withdrawing group from the viewpoint of safety. The electron withdrawing group preferably has a Hammett acidity value of larger than 0. The electron withdrawing group is preferably exemplified by halogen atom and carboxylic acid.

Other preferable sulfonium salt is exemplified by triarylsulfonium salt with one of the substituent thereof having a coumarin or anthraquinone structure, showing absorption in the region of 300 nm or longer. Still other preferable sulfonium salt is exemplified by triarylsulfonium salt having aryloxy group or arylthio group as a substituent, showing absorption in the region of 300 nm or longer.

The onium salt compound is exemplified by selenonium salt described in J. V. Crivello et al., *Macromolecules*, 10(6), 1307(1977), and J. V. Crivello et al., Jr. *Polymer Sci., Polymer Chem. Ed.*, 17, 1047(1979); and arsonium salt described in C. S. Wen et al., *Tech. Proc. Conf. Rad. Curing ASIA*, p. 478 Tokyo, October (1988).

The acylphosphine (oxide) compound is exemplified by Irgacure 819, Darocure 4265 and Darocure TPO, all from BASF.

Only a single species of photo-polymerization initiator may be used, or two or more species of them may be used in combination. The total content of the photo-polymerization initiators relative to the total solid content in the photo-sensitive resin composition is preferably 0.1 to 30% by mass, more preferably 0.5 to 20% by mass, even more preferably 1 to 8% by mass, and yet more preferably 1 to 5% by mass.

With the content of the photo-polymerization initiator controlled to 0.1% by mass or more, a good pattern may be formed. Meanwhile, if controlled to 30% by mass or less, the development residue may further be suppressed.

<Polymerizable Monomer>

The photo-sensitive resin composition of this invention contains at least one species of polymerizable monomer. As the polymerizable monomer, a compound having at least one ethylene double bond capable of participating in addition polymerization, and having a boiling point under normal pressure of 100° C. or higher is preferable, and a (meth) acrylate monomer having a boiling point under normal pressure of 100° C. or higher is more preferable.

By using the polymerizable monomer with the photo-polymerization initiator and so forth, the photo-sensitive resin composition of this invention will be configured to be negative type.

The monomer having a hydrogen bondable group (may also be referred to as "hydrogen bondable group-containing monomer", hereinafter) is more preferable.

More specifically, the hydrogen bondable group is exemplified by hydroxy group, carboxy group, amino group, ureido group, alkoxycarbonyl amino group, sulfo group, sulfonamido group, and amido group. Among them, those having both of a hydrogen atom which can be donated to the hydrogen bond, and a substituent capable of accepting the hydrogen bond, are preferable.

From the viewpoint of the rectangularity of pattern, the hydrogen bondable group is more preferably at least one species selected from carboxy group, alkoxycarbonylamino group, and ureido group.

The hydrogen bondable group-containing monomer is preferably multi-functional monomer (also referred to as "multi-functional polymerizable monomer", hereinafter).

Specific examples of the multi-functional polymerizable monomer containing the hydrogen bondable group will be explained below.

The multi-functional polymerizable monomer containing hydroxy group is exemplified by pentaerythritol triacrylate, dipentaerythritol hexaacrylate, ECH-modified ethylene glycol diacrylate, ECH-modified glycerol triacrylate, ECH-modified phthalic diacrylate, triglycerol diacrylate, and ECH-modified trimethylolpropane triacrylate.

The multi-functional polymerizable monomer containing carboxy group is exemplified by the compounds represented by Formula (III-1) or Formula (III-2) below. This invention is, however, not limited thereto.

When T or G in Formulae below represents an oxyalkylene group, the carbon atom terminal thereof is bound to R, X and W.

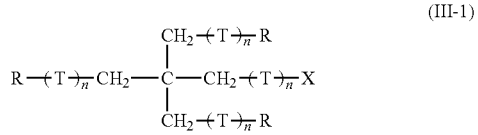

(III-1)

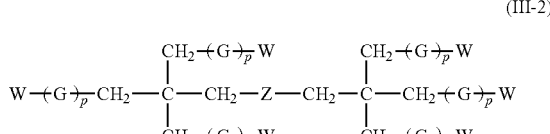

(III-2)

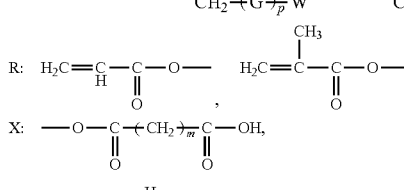

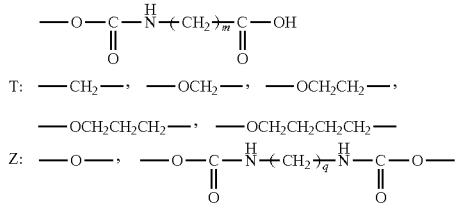

-continued

G: —CH$_2$—, —OCH$_2$—, —OCH$_2$CH$_2$—,

—OCH$_2$CH$_2$CH$_2$—, —OCH$_2$CH$_2$CH$_2$CH$_2$—

In Formula (III-1), n represents an integer of 0 to 14, and m represents an integer of 1 to 8. In Formula (III-2), W represents R or X synonymous to those in Formula (III-1), wherein among six (W)s, three or more and five or less (W)s represent R. p represents an integer of 0 to 14, and q represents an integer of 1 to 8. Each of plurality of (R)s, (X)s, (T)s and (G)s in one molecule are same or different.

Specific examples of the compounds represented by Formula (III-1) or Formula (III-2) may be referred to the description in paragraphs [0175] to [0179] of JP-A-2010-049029, the contents of which are incorporated into this specification.

Combinations of the multi-functional polymerizable monomer having a carboxy group explained above, and other monomers described later may be commercially available from Toagosei Co., Ltd. under the trade names of TO-2359, TO-2360, TO-2348 and TO-756.

The multi-functional monomer having an alkoxycarbonylamino group is exemplified by U-6LHA, U-6LYXA and U-12LMA from Shin-Nakamura Chemical Co., Ltd.

The multi-functional monomer having an amido group is exemplified by monomers M-315 and M-215 from Toagosei Co., Ltd.

Specific examples of the multi-functional monomers having other hydrogen bondable groups are referred to the description in paragraphs [0178] to [0182] of JP-A-2010-049029, the contents of which are incorporated into this specification.

Among the hydrogen bondable group-containing monomer described above, carboxy group-containing monomer, alkoxycarbonylamino group-containing monomer and ureido group-containing monomer are preferable, and carboxy group-containing monomer is particularly preferable.

With the content of the hydrogen bondable group-containing monomer controlled to 30% by mass or more relative to the total solid content, the photo-sensitive resin composition of this invention will be prevented from degrading in the rectangularity after post-baking. The content of the hydrogen bondable group-containing monomer, relative to the total solid content in the photo-sensitive resin composition of this invention, is preferably 33% by mass or more, and most preferably 35% by mass or more.

In this invention, as a monomer other than the above-described polymerizable monomer, the polymerizable monomer described in paragraph [0186] of JP-A-2010-049029 may be added, the contents of which are incorporated into this specification.

Among them, multi-functional (meth)acrylic compound is particularly preferable as the polymerizable monomer, and multi-functional (meth)acrylate having no hydrogen bondable group is most preferable.

The content of the polymerizable monomer in the photo-sensitive resin composition is preferably 10 to 80% by mass relative to the total solid content in the composition, more preferably 10 to 70% by mass, and most preferably 10 to 60% by mass. A good cured film may be obtained by controlling the total monomer content to 10% by mass or more, and the development residue may more effectively be suppressed by controlling the content to 80% by mass or less.

Only a single species of the polymerizable monomer may be used, or two or more species of them may be used. When two or more species are used, the total content preferably satisfies the amount of mixing described above.

Combination of the polymerizable monomer and the ultraviolet absorber represented by Formula (I), in the photo-sensitive resin composition of this invention, is preferably as described below, from the viewpoint of suitably balancing reduction in the development residue and improvement in the rectangularity of pattern.

That is, the preferable combination relates to embodiments in which the polymerizable monomer is a multi-functional monomer which contains at least one species of hydrogen bondable group selected from carboxy group, alkoxycarbonylamino group and ureido group, and the ultraviolet absorber is the compound represented by Formula (I).

Among these embodiments, those in which the photo-sensitive resin composition of this invention further contains, as the monomer, a multi-functional (meth)acrylate having no hydrogen bondable group, are particularly preferable.

<Resin>

It is preferable that the photo-sensitive resin composition of this invention optionally contains at least one species of resin without adversely affecting the effect of this invention. The resin is preferably a linear organic high molecular polymer.

The linear organic high molecular polymer is arbitrarily selectable from known ones. From the viewpoint of enabling development with water or weak alkaline aqueous solution, it is preferable to select a linear organic polymer which is soluble or swellable in water or weak alkaline aqueous solution. The linear organic polymer is selected and used, depending on applications using water, weak alkaline aqueous solution or organic solvent, as the developing agent. Among them, alkali-soluble resin is more preferable.

While the alkali-soluble resin is not specifically limited so long as it is alkali-soluble, it is preferable to select it taking heat-resistance, developability, and availability into consideration.

The alkali-soluble resin is preferably linear organic high molecular polymer, which is soluble in solvent and developable with weak alkaline aqueous solution. This sort of linear organic high molecular polymer is exemplified by polymers having carboxylic acid in the side chain thereof, such as methacrylic acid copolymer, acrylic acid copolymer, itaconic acid copolymer, crotonic acid copolymer, maleic acid copolymer, partially esterified maleic acid copolymer, as described in JP-A-S59-44615, JP-B-S54-34327, JP-B-S58-12577, JP-B-S54-25957, JP-A-S59-53836, and JP-A-S59-71048. Also acidic cellulose derivatives, again having carboxylic acid in the side chain thereof, are useful.

Besides those described above, as the alkali-soluble resin, also hydroxy group-containing polymer added with acid anhydride, polyhydroxystyrene-based resin, polysiloxane-based resin, poly(2-hydroxyethyl(meth)acrylate), polyvinylpyrrolidone, polyethylene oxide, and polyvinyl alcohol are useful.

The linear organic high molecular polymer may alternatively be co-polymerized with a hydrophilic monomer. Examples of the monomer include alkoxyalkyl(meth)acrylate, hydroxyalkyl(meth)acrylate, glycerol (meth)acrylate, (meth)acrylamide, N-methylol acrylamide, secondary or tertiary alkylacrylamide, dialkylaminoalkyl (meth)acrylate, morpholine (meth)acrylate, N-vinylpyrrolidone, N-vinylcaprolactam, vinylimidazole, vinyltriazole, methyl (meth)acrylate, ethyl (meth)acrylate, branched or straight-chain propyl (meth)acrylate, branched or straight-chain butyl (meth)acrylate, and phenoxyhydroxypropyl (meth)acrylate.

Note that, in this specification, (meth)acrylate represents acrylate or methacrylate, (meth)acryl represents acryl or methacryl, and (meth)acrylamide represents acrylamide or methacrylamide.

Beside those described above, also monomers containing tetrahydrofuryl group, phosphate group, phosphate ester group, quaternary ammonium salt group, ethylenoxy chain, propyleneoxy chain, groups derived from sulfonic acid or salt thereof, and morpholino group, are usable as the hydrophilic monomer.

In view of improving efficiency of crosslinking, it is particularly preferable that the alkali-soluble resin has a polymerizable group in the side chain thereof. For example, polymers having allyl group, (meth)acryl group, or acryloxyalkyl group in the side chains thereof are useful.

Examples of the polymer having polymerizable group include commercially available KS Resist-106 (from Osaka Organic Chemical Industry, Ltd.), and Cyclomer P Series (Cyclomer P-ACA, etc., from Daicel Corporation). Aimed at improving the strength of the cured film, also polyethers formed between alcohol-soluble nylon or 2,2-bis-(4-hydroxyphenyl)-propane, with epichlorohydrin are useful.

Among these alkali-soluble resins, preferable examples from the viewpoint of heat resistance include polyhydroxystyrene-based resin, polysiloxiane-based resin, acryl-based resin, acrylamide-based resin and acryl/acrylamide copolymer resin; and preferable examples from the viewpoint of controlling the developability include acryl-based resin, acrylamide-based resin and acryl/acrylamide copolymer resin.

Preferable examples of the acryl-based resin includes copolymers obtained by polymerizing a monomer selected from benzyl (meth)acrylate, (meth)acrylic acid, hydroxyethyl (meth)acrylate, and (meth)acrylamide; and commercially available KS Resist-106 (from Osaka Organic Chemical Industry, Ltd.), Cyclomer P Series (from Daicel Corporation), and Acrybase FF-187 (from Fujikura Kasei Co., Ltd.).

From the viewpoints of developability and viscosity of solution, the alkali-soluble resin is preferably a polymer having a weight-average molecular weight (polystyrene equivalent value measured by GPC) of 1000 to $2 \times 10^5$, more preferably 2000 to $1 \times 10^5$, and even more preferably 5000 to $5 \times 10^4$.

In this invention, from the viewpoint of developability, the content of the resin in the photo-sensitive resin composition is preferably 10 to 90% by mass relative to the total solid content in the photo-sensitive resin composition, more preferably 20 to 60% by mass, and particularly 25 to 50% by mass.

Only a single species of resin may be used, or two or more species may be used in combination. When two or more species are used, the total content preferably satisfies the amount of addition described above.

<Particle>

The photo-sensitive resin composition of this invention may contain a particle. The particle used in this invention preferably has a refractive index at 500 nm of 1.64 or larger (may be referred to as "high-refractive-index particle", hereinafter), more preferably 1.80 to 3.0, and even more preferably 1.80 to 2.80. With the refractive index of the high-refractive-index particle controlled in these ranges, the refractive index may advantageously be increased while keeping the variability of transmittance of the cured film within a specific range. Meanwhile, with the lower value controlled to the above-described value or larger, interference with pixels of other colors may suitably be suppressed or prevented.

The high-refractive-index particle preferably has a weight-average diameter of primary particle of 150 nm or smaller, more preferably 100 nm or smaller, and particularly 80 nm or smaller. While the lower limit value is not specifically limited, it is practically 1 nm or larger. The weight-average diameter of the high-refractive-index particle in the layer is preferably 200 nm or smaller, more preferably 150 nm or smaller, even more preferably 100 nm or smaller, and particularly 80 nm or smaller. While the lower limit value is not specifically limited, it is preferably 1 nm or larger, more preferably 5 nm or larger, and even more preferably 10 nm or larger. The reason why the range of particle size of the primary particle is different from that in the layer is that aggregation of the primary particle in the layer was taken into account. The weight-average diameter of the high-refractive-index particle is measured referring to Japanese Industrial Standards (JIS K 0062:1992), stating a method of measuring refractive index of substances composing the high-refractive-index particle, unless otherwise specifically noted.

The high-refractive-index particle is exemplified by particles which contain metal oxide having at least one species of element selected from Ti, Zr, Sn, Sb, Cu, Fe, Mn, Pb, Cd, As, Cr, Hg, Zn, Al, Mg, Si, P and S. Specific examples include particles of titanium dioxide, tin oxide, indium oxide, zinc oxide and zirconium oxide. Among them, particles of titanium dioxide, tin oxide, indium oxide, and zirconium oxide are particularly preferable, and particles of titanium dioxide and zirconium oxide are more preferable.

The metal oxide particle, containing any of these metal oxides as a major ingredient, may contain other additional element. The major ingredient means the ingredient whose content (% by mass) is largest among all ingredients composing the particle. Such other element is exemplified by Ti, Zr, Sn, Sb, Cu, Fe, Mn, Pb, Cd, As, Cr, Hg, Zn, Al, Mg, Si, P and S. As for the crystal structure of inorganic fine particle mainly composed of titanium dioxide, rutile, rutile-anatase mixed structure, anatase or amorphous preferably prevails, among which the rutile structure is preferable.

The high-refractive-index particle is preferably surface-treated. The surface treatment may be given using inorganic compound or organic compound. The inorganic compound used for the surface treatment is exemplified by alumina, silica, zirconium oxide and iron oxide. Among them, alumina and silica are preferable. The organic compound used for the surface treatment is exemplified by polyol, alkanolamine, stearic acid, silane coupling agent and titanate coupling agent.

As one typical embodiment of this invention, exemplified is an inorganic particle mainly composed of titanium dioxide, and containing at least one element selected from Co (cobalt), Al (aluminum) and Zr (zirconium). Accordingly, the photocatalytic activity intrinsic to titanium dioxide may be suppressed, and thereby weatherability of the high-refractive-index layer may be improved effectively.

The high-refractive-index particle may be surface-treated by a combination of two or more types of surface treatment. The metal oxide particle is preferably shaped in rice grain, sphere, cube, spindle or irregular shape. Two or more species of metal oxide particles may be used together in the high-refractive-index layer and middle-refractive-index layer.

The total content of the high-refractive-index particles in the composition is preferably 10% by mass or more relative to the total solid content, more preferably 15% by mass or more, and even more preferably 15% by mass or more. The upper limit is preferably 50% by mass or less, more preferably 40% by mass or less, and particularly 35% by mass or less.

The high-refractive-index particle used in this invention is preferably mixed in the form of a dispersed composition to the photo-sensitive resin composition. The detail may be referred to the description of JP-A-2007-277514. For the dispersion, it is particularly preferable to use the dispersed resin described in Examples in JP-A-2007-277514.

<Dye and/or Pigment>

While the photo-sensitive resin composition of this invention does not necessarily contain any colorant (known dyes and pigments, and black materials such as carbon black or titanium black) when clear (translucent) pattern is used, it contains dye and/or pigment when patterns such as in red, blue, green and so forth are formed. Only a single species of the dye and/or pigment may be used, or two or more species of them may be used in combination.

The pigment is exemplified by those described in paragraphs [0030] to [0044] of JP-A-2008-224982, and those obtained by replacing Cl substituents of C.I. Pigment Green 58 and C.I. Pigment Blue 79 with OH groups. Among them, preferable examples are enumerated below. This invention is, however, not limited thereto.

C.I. Pigment Yellow 11, 24, 108, 109, 110, 138, 139, 150, 151, 154, 167, 180, 185;

C.I. Pigment Orange 36;

C.I. Pigment Red 122, 150, 171, 175, 177, 209, 224, 242, 254, 255;

C.I. Pigment Violet 19, 23, 29, 32;

C.I. Pigment Blue 15:1, 15:3, 15:6, 16, 22, 60, 66;

C.I. Pigment Green 7, 36, 37, 58;

C.I. Pigment Black 1

The dye is arbitrarily selectable from known dyes, without special limitation. The dye is exemplified by those described in JP-A-S64-90403, JP-A-S64-91102, JP-A-H01-94301, JP-A-H06-11614, Japanese Patent No. 2592207, U.S. Pat. No. 4,808,501, U.S. Pat. No. 5,667,920, U.S. Pat. No. 5,059,500, JP-A-H05-333207, JP-A-H06-35183, JP-A-H06-51115, JP-A-H06-194828, JP-A-H08-211599, JP-A-H04-249549, JP-A-H10-123316, JP-A-H11-302283, JP-A-H07-286107, JP-A-2001-4823, JP-A-H08-15522, JP-A-H08-29771, JP-A-H08-146215, JP-A-H11-343437, JP-A-H08-62416, JP-A-2002-14220, JP-A-2002-14221, JP-A-2002-14222, JP-A-2002-14223, JP-A-H08-302224, JP-A-H08-73758, JP-A-H08-179120 and JP-A-H08-151531.

From the viewpoint of chemical structure, dyes having pyrazoleazo-based, anilinoazo-based, triphenylmethane-based, anthraquinone-based, anthrapyridone-based, benzylidene-based, oxonol-based, pyrazolotriazolazo-based, pyridoneazo-based, cyanine-based, phenothiazine-based, pyrrolopyrazoleazomethine-based, xanthene-based, phthalocyanine-based, benzopyran-based, and indigo-based structures may be used.

The total content of the dye and/or pigment, when contained in the photo-sensitive composition of this invention, is preferably 0.1 to 20% by mass relative to the total solid content in the composition, and more preferably 1 to 18% by mass.

<Solvent>

The photo-sensitive resin composition of this invention may generally be configured by using solvent.

While the solvent is not specifically limited in principle, so long as solubility of the individual ingredients, and coatability of the photo-sensitive resin composition are suitably satisfied, the solvent is generally organic solvent, which is preferably selected taking in particular solubility of the ultraviolet absorber and binder, coatability and safety into consideration. For preparation of the photo-sensitive resin composition of this invention, only a single species of solvent may be used, or two or more species of solvents may be used.

The solvent may be referred to the description in paragraphs [0190] to [0194] of JP-A-2010-049029, the contents of which are incorporated into this specification.

In particular in this invention, the solvent is preferably selectable from methyl 3-ethoxypropionate, ethyl 3-ethoxypropionate (ethoxy propionate), ethylcellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol monomethyl ether acetate.

The content of the solvent in the photo-sensitive resin composition is preferably controlled so that the total solid concentration in the composition will be 5 to 90% by mass from the viewpoint of coatability, more preferably 5 to 87% by mass, and particularly 10 to 85% by mass.

<Other Additives>

To the photo-sensitive resin composition of this invention, various additives, such as sensitizer, polymerization inhibitor, adhesion enhancer, surfactant, filler, polymer compound other than those described above, antioxidant, and deflocculating agent may optionally be added. Only one species of these additives may be used, or two or more species may be used.

<<Sensitizer>>

The composition of this invention may contain sensitizer, for the purpose of improving radical generation efficiency of the polymerization initiator, and shifting the photo-sensitive wavelength towards the longer region. The sensitizer is preferably any of those capable of sensitizing the polymerization initiator, used in combination, based on an electron transfer mechanism or energy transfer mechanism. Preferable examples of the sensitizer are exemplified by the compounds described in paragraphs [0085] to [0098] of JP-A-2008-214395. The content of the sensitizer is preferably 0.1 to 30% by mass relative to the total solid content in the composition, from the viewpoint of sensitivity and shelf stability, more preferably 1 to 20% by mass, and even more preferably 2 to 15% by mass.

<<Polymerization Inhibitor>>

In the process of manufacture and storage of the composition of this invention, it is preferable to add a small amount of polymerization inhibitor in order to prevent unnecessary thermal polymerization of the polymerizable compound. The polymerization inhibitor may be any of known thermal polymerization inhibitors, and is specifically exemplified by hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitorosophenylhydroxyamine serium(III) salt.

The amount of addition of the thermal polymerization inhibitor is preferably approx. 0.01 to approx. 5% by mass relative to the total solid content in the composition.

Alternatively, in order to prevent inhibition of polymerization by oxygen, it is optionally possible to add behenic acid, or a higher fatty acid derivative such as behenic acid amide, and allow it to more dominantly distribute on the surface of the coated film in the process of drying after coating. The content of the higher fatty acid derivative is preferably approx. 0.5 to approx. 10% by mass relative to the total solid content in the composition.

<<Adhesion Enhancer>>

For the purpose of improving the adhesiveness to a hard surface such as support, an adhesion enhancer may be added to the composition of this invention. The adhesion enhancer is exemplified by silane-based coupling agent and titanium coupling agent.

The silane-based coupling agent is preferably exemplified by γ-methacryloxypropyl trimethoxysilane, γ-methacryloxypropyl triethoxysilane, γ-acryloxypropyl trimethoxysilane, γ-acryloxypropyl triethoxysilane, γ-mercaptopropyl trimethoxysilane, 3-methacryloxypropyl dimethoxymethylsilane, γ-aminopropyl triethoxysilane, and phenyl trimethoxysilane, and more preferably exemplified by γ-methacryloxypropyl trimethoxysilane, and 3-methacryloxypropyl dimethoxymethylsilane.

The amount of addition of the adhesion enhancer is preferably 0.5 to 30% by mass relative to the total solid content in the composition, and more preferably 0.7 to 20% by mass.

<<Surfactant>>

From the viewpoint of further improving the coatability, various types of surfactant may be added to the composition of this invention. Various types of surfactants such as fluorine-containing surfactant, nonionic surfactant, cationic surfactant, anionic surfactant, and silicone-based surfactant may be used as the surfactant.

In particular, as a result of incorporation of the fluorine-containing surfactant, the composition according to preferable embodiments of this invention will have an improved liquid property (in particular, fluidity) when prepared in the form of coating liquid, and thereby the uniformity in thickness of the coated film and liquid saving property may further be improved.

More specifically, when the film is formed using a coating liquid applied with the composition containing the fluorine-containing surfactant, the interfacial tension between the surface to be coated and the coating liquid may be reduced, the wetting on the surface to be coated may be improved, and thereby the coatability on the surface to be coated may be improved. This is advantageous in that the film having a uniform thickness, only with a small variation of thickness, may be obtained even when a thin film of several micrometers thick or around is formed using a small volume of liquid.

The fluorine content in the fluorine-containing surfactant is preferably 3% by mass to 40% by mass, more preferably 5% by mass to 30% by mass, and particularly 7% by mass to 25% by mass. The fluorine-containing surfactant having the fluorine content controlled in these ranges is effective in terms of uniformity in thickness of the coated film and liquid saving property, and shows a good solubility in the composition.

The fluorine-containing surfactant is exemplified by Megafac F171, ditto F172, ditto F173, ditto F176, ditto F177, ditto F141, ditto F142, ditto F143, ditto F144, ditto R30, ditto F437, ditto F475, ditto F479, ditto F482, ditto F554, ditto F780, ditto F781 (all from DIC Corporation); Fluorad FC430, ditto FC431, ditto FC171 (all from Sumitomo 3M Ltd.); Surflon S-382, ditto SC-101, ditto SC-103, ditto SC-104, ditto SC-105, ditto SC1068, ditto SC-381, ditto SC-383, ditto 5393, ditto KH-40 (all from Asahi Glass Co., Ltd.); and Solsperse 20000 (from Lubrizol Japan Ltd.).

Other examples of the surfactant may be referred to the description in paragraphs [0485] to [0489] of JP-A-2013-045088, the contents of which are incorporated into this specification.

Only one species of the surfactant may be used, or two or more species may be used in combination. The amount addition of the surfactant is preferably 0.001% by mass to 2.0% by mass relative to the total solid content in the composition, and more preferably 0.005% by mass to 1.0% by mass.

Other additives usable here may be those described in paragraphs [0382] and [0383], the contents of which are incorporated into this specification.

<Method for Forming Pixels>

Method for forming pixels of this invention includes coating the photo-sensitive resin composition of this invention, exposing the formed layer with ultraviolet radiation through a photomask, developing the layer to form a pattern, and post-baking the formed pattern.

Methods of coating, applicable to coating the photo-sensitive resin composition of this invention to form a layer, include slit coating, ink jet process, spin coating, cast coating, roll coating and screen printing.

The thickness of the layer composed of the photo-sensitive resin composition is preferably 0.1 μm to 10 μm, more preferably 0.2 μm to 5 μm, and even more preferably 0.2 μm to 3 μm.

The layer composed of the photo-sensitive resin composition may be dried (pre-baked), for example, on a hot plate or in an oven, at 50° C. to 140° C. for 10 seconds to 300 seconds.

In the exposing the thus formed layer with at least ultraviolet radiation through a photomask, the layer is exposed pattern-wise, typically by using an exposure apparatus such as stepper, through a mask having a predetermined mask pattern.

Radial ray (light) usable for the exposure is preferably ultraviolet radiation such as g-line and i-line, and more preferably i-line. The irradiation dose (exposure dose) is preferably 30 to 1500 mJ/cm$^2$, more preferably 50 to 1000 mJ/cm$^2$, and particularly 80 to 500 mJ/cm$^2$.

The development for forming a pattern is preferably implemented by alkali development. By the process, a portion of the photo-sensitive resin composition layer, remained unexposed in the exposure step, dissolves into an aqueous alkali solution, and only a photo-cured portion remains.

The developing solution is preferably an organic alkali developing solution which does not damage the underlying imaging devices and circuits. The temperature of development has generally been set to 20° C. to 30° C., and the time of development has been set to 20 seconds to 90 seconds. For more thorough removal of the residue, some recent process has employed a development time of 120 seconds to 180 seconds. Another known process has further improved the removability of residue, by spinning off the developing solution and feeding the fresh liquid, which are repeated every 60 seconds and several times.

The alkali agent used as the developing solution is exemplified by organic alkali compounds such as ammonia water, ethylamine, diethylamine, dimethylethanolamine, tetramethylammonium hydroxide, tetraethylammonium hydroxide, choline, pyrrole, piperidine, and 1,8-diazabicyclo-[5,4,0]-7-undecene. These alkali agents are diluted with pure water so as to control the concentration of alkali agent to 0.001 to 10% by mass, and preferably 0.01 to 1% by mass to give alkali aqueous solution, and are preferably used as the developing solution.

Also inorganic alkali may be used for the developing solution. The inorganic alkali is preferably exemplified by sodium hydroxide, potassium hydroxide, sodium carbonate, sodium hydrogen carbonate, sodium silicate, and sodium metasilitcate.

When the developing solution composed of such alkali aqueous solution was used, the development is generally followed by rinsing with pure water.

The layer is then dried, which is preferably followed by heating (post-baking). For the case where a multi-colored pattern is formed, the method may be repeated successively for the individual colors, to form the cured film. The color filter may be obtained in this way.

The post-baking is a post-exposure heating process for completing the curing, and is generally implemented by heat curing at 100° C. to 350° C., and preferably 200° C. to 340° C.

In the post baking, the coated film after developed may be baked using a heating means such as hot plate, convection oven (hot air circulating drier), radio heater or the like, according to the conditions described above, in a continuous manner or batch manner.

<Color Filter>

The color filter of this invention has pixels formed by the method of forming pixels described above.

The term "color" in the context of the color filter of this invention is construed to cover color in the broad sense, and conceptionally cover not only chromatic color such as red, blue, green and so forth, but also achromatic color such as clear. In other words, a pattern of the color filter of this invention may be a chromatic pattern in red, blue, green or the like, or may be an achromatic pattern in clear or the like.

The color filter of this invention may be a combination of at least one chromatic pattern in red, blue, green or the like, with at least one achromatic pattern in clear or the like. This sort of color filter is exemplified by the one having a red pattern (red pixels), a blue pattern (blue pixels), a green pattern (green pixels), and a clear pattern (clear pixels).

The photo-sensitive resin composition of this invention described above is used for forming pixels of a solid state image sensor (in particular, clear pixels composing clear pattern).

From the viewpoint of suitably using for such application, the photo-sensitive resin composition of this invention when made into a 1-μm thick film preferably has a transmittance of 80% or larger (more preferably 85% or larger) over the entire wavelength range from 400 nm to 700 nm. The cured film of this invention, in which the ultraviolet absorber represented by Formula (I) has been decomposed, may typically have a content of the ultraviolet absorber represented by Formula (I) of 0.01% by mass or less relative to the cured film, and may further contain substantially no ultraviolet absorber.

<Solid State Image Sensor>

The solid state image sensor of this invention has the color filter of this invention.

The solid state image sensor of this invention is equipped with the color filter of this invention, featured by its good rectangularity of the pixels (patterns), and therefore has a good color reproducibility.

Configuration of the solid state image sensor of this invention is not specifically limited, so long as it is configured to have the color filter of this invention, and can function as a solid state image sensor. Exemplary configurations are as follows.

In one configuration, on a support, there are provided a plurality of photodiodes which configure a light receiving area of a solid state image sensor (for example, CCD image sensor or CMOS image sensor) and transfer electrodes typically composed of polysilicon; a shading film typically made of tungsten or the like, covering the photodiodes and the transfer electrodes but opened only over the light receiving area of the photodiodes; a device protective film typically made of silicon nitride, formed so as to cover the entire surface and the light receiving area of the photodiodes; and the color filter of this invention provided on the device protective film.

Another configuration may additionally have a light condensing means (for example, microlenses or the like), on the device protective and under the color filter (on the side closer to the support); and still another configuration may have a light condensing means on the color filter.

<Liquid Crystal Display Device>

The liquid crystal display device of this invention has the color filter of this invention. Details of the liquid crystal display device may be referred to the description in paragraphs [0399] to [0403] of JP-A-2012-215806, the contents of which are incorporated into this specification.

EXAMPLE

This invention will further be detailed below referring to Examples, to which this invention is not limited without departing from the spirit thereof. All "part (s)" and "%" are given on the mass basis, unless otherwise specifically noted.

Exemplary Synthesis 1

Method of Synthesis of Exemplary Compound 1

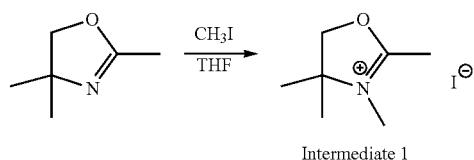

Intermediate 1

2,2,2-Trimethyl-2-oxazoline (70.8 g), triiodomethane (118 g), and THF (80 ml) were placed in a flask, and the content was stirred for 15 hours. A crystal deposited from the reaction solution was collected by filtration. The crystal was dried at 50° C. under air flow, to obtain 126 g of Intermediate 1.

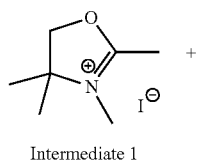

Intermediate 1

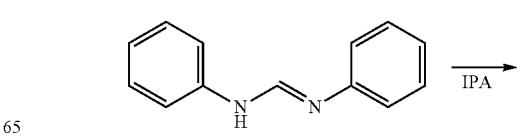

-continued

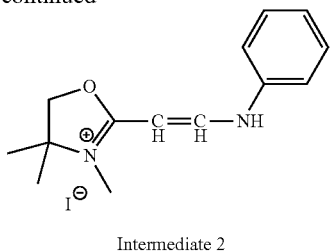

Intermediate 2

Intermediate 1 (133 g), N,N'-diphenylformamidine (103 g), and IPA (350 ml) were placed in a flask, and the content was stirred at 90° C. for 6 hours. A crystal deposited from the reaction solution was collected by filtration. The crystal was dried at 50° C. under air flow, to obtain 151 g of Intermediate 2.

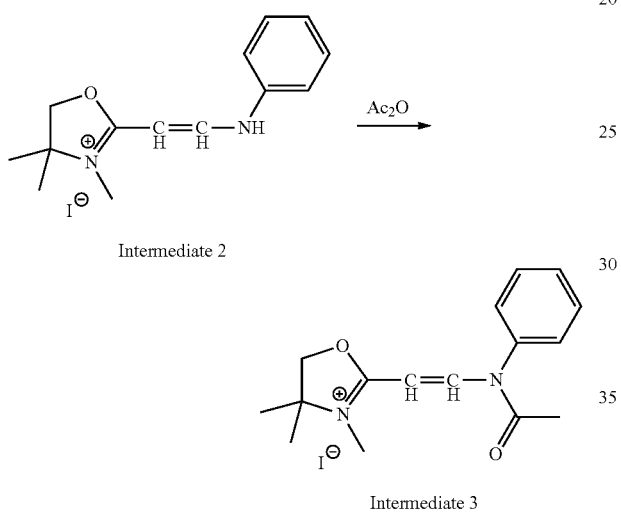

Intermediate 2 (151 g) and acetic anhydride (400 ml) were placed in a flask, and the content was stirred at 120° C. for 2 hours. A crystal deposited from the reaction liquid was collected by filtration. The crystal was dried at 50° C. under air flow, to obtain 149 g of Intermediate 3.

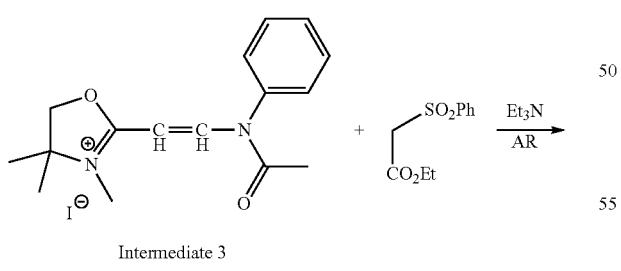

Intermediate 3 (5.0 g), ethyl phenylsulfonylacetate (3.0 g), triethylamine (1.2 g) and acetonitrile (20 ml) were placed in a flask, and the content was stirred at 60° C. for 5 hours. Acetonirile was removed, the residue was purified by column chromatography, and the eluate was recrystallized from ethanol to obtain a target product. The crystal was dried at 50° C. under air flow, to obtain 3.0 g of Exemplary Compound 1.

λmax=367 nm (ethyl acetate (AcOEt))

$^1$H-NMR (CDCl$_3$) δ: 8.50 (d, 1H), 7.91 (d, 2H), 7.44 (m, 3H), 6.00 (d, 1H), 4.26 (s, 2H), 4.06 (q, 2H), 2.89 (s, 3H), 1.37 (s, 6H), 1.07 (t, 3H)

Exemplary Synthesis 2

Method of Synthesizing Exemplary Compound 2

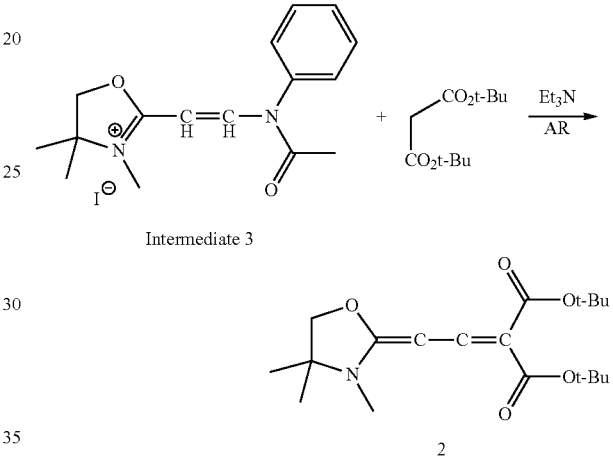

Intermediate 3 (16 g), di(t-butyl) malonate (17 g), triethylamine (7.9 g) and acetonitrile (60 ml) were placed in a flask, and the content was stirred at 100° C. for 5 hours. Acetonirile was removed, the residue was purified by column chromatography, and the eluate was recrystallized from ethanol to obtain a target product. The crystal was dried at 50° C. under air flow, to obtain 3.7 g of Exemplary Compound 2.

λmax=371 nm (AcOEt)

$^1$H-NMR (CDCl$_3$) δ: 7.96 (d, 1H), 5.32 (d, 1H), 4.09 (s, 2H), 2.76 (s, 3H), 1.53 (s, 9H), 1.59 (s, 9H), 1.27 (s, 6H)

Exemplary Synthesis 3

Method of Synthesizing Exemplary Compound 3

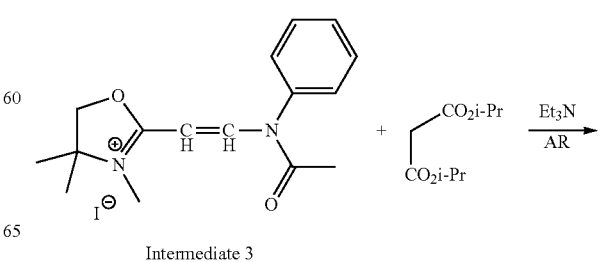

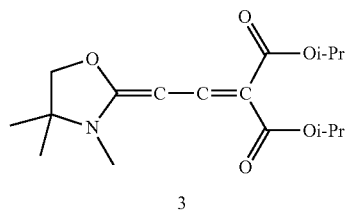

3

Intermediate 3 (15 g), di(isopropyl) malonate (7.2 g), triethylamine (3.6 g) and acetonitrile (60 ml) were placed in a flask, and the content was stirred at 65° C. for 2 hours. Acetonirile was removed, the residue was purified by column chromatography, and the eluate was recrystallized from ethanol to obtain a target product. The crystal was dried at 50° C. under air flow, to obtain 6.0 g of Exemplary Compound 3.

λmax=365 urn (AcOEt)
$^1$H-NMR (CDCl$_3$) δ: 8.14 (d, 1H), 5.63 (d, 1H), 5.11 (m, 2H), 4.14 (s, 2H), 2.80 (s, 3H), 1.25 (m, 18H)

Exemplary Synthesis 4

Method of Synthesizing Exemplary Compound 4

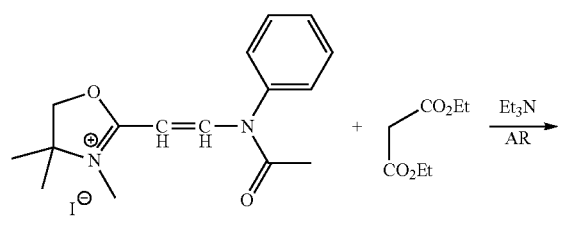

Intermediate 3

4

Intermediate 3 (5.0 g), diethyl malonate (2.1 g), triethylamine (1.2 g) and acetonitrile (20 ml) were placed in a flask, and the content was stirred at 50° C. for 7 hours. Acetonitrile was removed, the residue was purified by column chromatography, and the eluate was recrystallized from ethanol to obtain a target product. The crystal was dried at 50° C. under air flow, to obtain 1.8 g of Exemplary Compound 4.

λmax=364 nm (AcOEt)
$^1$H-NMR (CDCl$_3$) δ: 8.24 (d, 1H), 5.74 (d, 1H), 4.17 (s, 2H), 4.23 (m, 4H), 2.83 (s, 3H), 1.31 (s, 6H), 1.32 (m, 6H)

Exemplary Synthesis 5

Method of Synthesizing Exemplary Compound 5

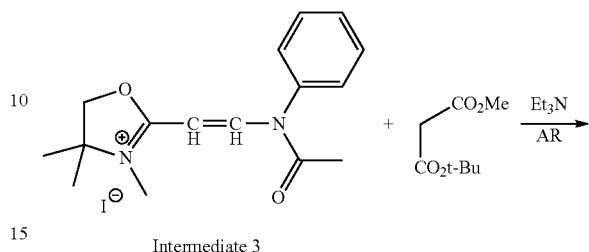

Intermediate 3

5

Intermediate 3 (5.0 g), t-butyl acetoacetate (2.1 g), triethylamine (1.2 g) and acetonitrile (20 ml) were placed in a flask, and the content was stirred at 50° C. for 7 hours. Acetonitrile was removed, the residue was purified by column chromatography, and the eluate was recrystallized from ethanol to obtain a target product. The crystal was dried at 50° C. under air flow, to obtain 2.8 g of Exemplary Compound 5.

λmax=386 nm (AcOEt)
$^1$H-NMR (DMSO) δ: 8.28 (d, 1H), 6.38 (d, 1H), 4.19 (s, 2H), 2.86 (s, 3H), 2.43 (s, 3H), 1.52 (s, 9H), 1.32 (s, 6H), 5:8.12 (d, 1H), 5.68 (d, 1H), 4.18 (s, 2H), 2.85 (s, 3H), 2.38 (s, 3H), 1.52 (s, 9H), 1.32 (s, 3H) (mixture of geometrical isomers).

Exemplary Synthesis 6

Method of Synthesizing Exemplary Compound 6

Intermediate 3

6

Intermediate 3 (5.0 g), ethyl acetoacetate (1.6 g), triethylamine (1.3 g) and acetonitrile (50 ml) were placed in a flask, and the content was stirred at 50° C. for 2 hours. Acetonitrile was removed, the residue was purified by column chromatography, and the eluate was recrystallized from ethanol to obtain a target product. The crystal was dried at 50° C. under air flow, to obtain 0.7 g of Exemplary Compound 6.

λmax=386 nm (AcOEt)

$^1$H-NMR (DMSO) δ: 8.15 (d, 1H), 5.64 (d, 1H), 4.36 (s, 2H), 4.08 (q, 2H), 2.88 (s, 3H), 2.23 (s, 3H), 1.31 (s, 6H), 1.20 (t, 3H), δ: 8.02 (d, 1H), 6.47 (d, 1H), 4.35 (s, 2H), 4.08 (q, 2H), 2.88 (s, 3H), 2.26 (s, 3H), 1.31 (s, 6H), 1.20 (t, 3H) (mixture of geometrical isomers).

Exemplary Synthesis 7

Method of Synthesis of Exemplary Compound 7

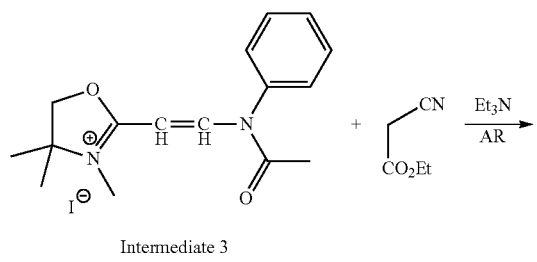

Intermediate 3

7

Intermediate 3 (5.0 g), ethyl cyanoacetate (1.5 g), triethylamine (1.3 g) and acetonitrile (20 ml) were placed in a flask, and the content was stirred at 50° C. for 3 hours. Acetonitrile was removed, the residue was purified by column chromatography, and the eluate was recrystallized from ethanol to obtain a target product. The crystal was dried at 50° C. under air flow, to obtain 2.0 g of Exemplary Compound 7.

λmax=372 nm (AcOEt)

$^1$H-NMR (CDCl$_3$) δ: 8.01 (d, 1H), 4.90 (d, 1H), 4.38 (s, 2H), 4.10 (q, 4H), 2.93 (s, 3H), 1.32 (s, 6H), 1.19 (t, 6H)

Exemplary Synthesis 8

Method of Synthesis of Exemplary Compound 8

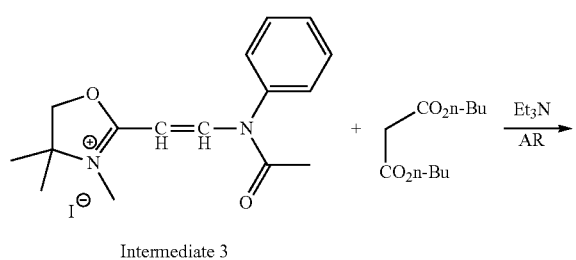

Intermediate 3

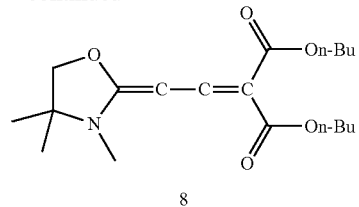

8

Intermediate 3 (16 g), dibutylmalonate (17 g), triethylamine (7.9 g) and acetonitrile (60 ml) were placed in a flask, and the content was stirred at 100° C. for 4 hours. Acetonitrile was removed, the residue was purified by column chromatography, and the eluate was recrystallized from ethanol to obtain a target product. The crystal was dried at 50° C. under air flow, to obtain 3.2 g of Exemplary Compound 8.

λmax=370 nm (AcOEt)

$^1$H-NMR (CDCl$_3$) δ: 7.95 (d, 1H), 5.31 (d, 1H), 4.07 (s, 2H), 4.22 (s, 4H), 2.74 (s, 3H), 1.62-1.35 (m, 8H), 1.27 (s, 6H), 1.02 to 0.83 (m, 6H)

Exemplary Synthesis 9

Method of Synthesizing Exemplary Compound 9

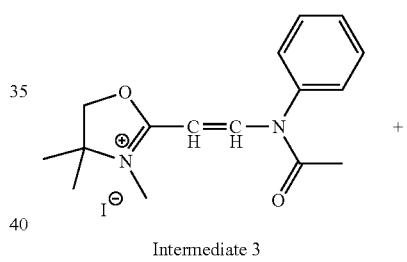

Intermediate 3

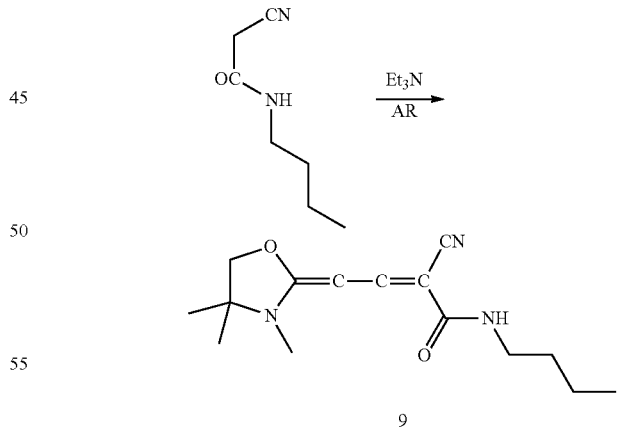

9

Intermediate 3 (5.0 g), N-butyl-2-cianoacetamide (2.1 g), triethylamine (1.3 g) and acetonitrile (50 ml) were placed in a flask, and the content was stirred at 50° C. for 5 hours. Acetonitrile was removed, the residue was purified by column chromatography, and the eluate was recrystallized from ethanol to obtain a target product. The crystal was dried at 50° C. under air flow, to obtain 1.4 g of Exemplary Compound 9.

λmax=369 nm (AcOEt)

$^1$H-NMR (CDCl$_3$) δ: 8.30 (d, 1H), 5.96 (s, 1H), 4.84 (d, 2H), 4.18 (s, 2H), 3.32 (q, 2H), 2.83 (s, 3H), 1.51 (m, 2H), 1.36 (m, 2H), 1.33 (s, 6H), 0.92 (t, 3H)

Example 1

Formation of Clear Pattern of Color Filter for Solid State Image Sensor

Preparation of Resist Liquid for Forming Planarizing Film

The ingredients below were mixed and stirred using a homogenizing stirrer to prepare a resist liquid for forming planarizing film.

~Composition of Resist Liquid for Forming Planarizing Film~

Propylene glycol monomethyl ether acetate solution of benzyl methacrylate/methacrylic acid (=70/30 [molar ratio]) copolymer (20%, weight-average molecular weight=30000, from Fujikura Kasei Co., Ltd., trade name: Acrybase FF-187) 22 parts Dipentaerythritol hexaacrylate (from Nippon Kayaku Co., Ltd., trade name: Kayarad DPHA) 6.5 parts Propylene glycol monomethyl ether acetate (from Daicel Corporation, trade name: MMPGAC) 13.8 parts Ethyl-3-ethoxy propionate (from Nagase & Co., Ltd., trade name: ethyl-3-ethoxy propionate) 12.3 parts Halomethyltriazine compound (Compound A below) (from Panchim S.A., trade name: triazine PP) 0.3 parts

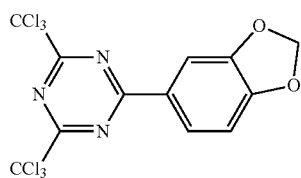

Compound A

<Formation of Planarizing Film>

The resist liquid for forming planarizing film obtained above was spin-coated over a 6-inch silicon wafer. The work was heated on a hot plate at a surface temperature of 100° C. for 120 seconds, to obtain a uniform coated film of approximately 0.1 μm thick on the silicon wafer. The coated film was then cured in an oven at 230° C. for one hour, to obtain a planarizing film.

<Preparation of Titanium Dioxide Dispersion Liquid>

A mixed liquid having the composition below was dispersed using a circulation disperser (bead mill), under the trade name of Ultra Apex Mill from Kotobuki Industries Co., Ltd., to obtain a titanium dioxide dispersion liquid.

~Composition of Titanium Dioxide Dispersion Liquid~

| | |
|---|---|
| Titanium dioxide (from Ishihara Sangyo Kaisha, Ltd., trade name: TTO-51(C)) | 212.5 parts |
| Specific dispersion resin (A) (20% solution in propylene glycol monomethyl ether acetate (abbreviated as "PGMEA", hereinafter)) | 286.9 parts |
| PGMEA | 350.6 parts |

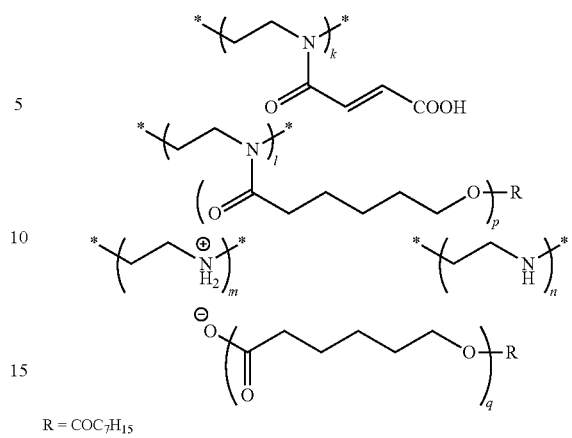

R = COC$_7$H$_{15}$

Specific dispersion resin (A)

In Specific dispersion resin (A), k:l:m:n=25:40:5:30 (molar ratio of polymerization), p=60, q=60, and weight-average molecular weight is 10,000. Specific dispersion resin (A) was prepared according to the description of JP-A-2007-277514.

The disperser was operated under the conditions below:
Bead diameter μ: 0.05 mm
Ratio of filling of beads: 75% by volume
Peripheral speed: 8 m/sec
Amount of feed by pump: 10 kg/hour
Cooling water: tap water
Inner volume of circulation passage of bead mill: 0.15 L
Volume of mixed liquid to be dispersed: 0.44 kg <Preparation of Photo-Sensitive Resin Composition>

The ingredients below were stirred and mixed using a magnetic stirrer, to prepare a photo-sensitive resin composition.

~Composition of Photo-Sensitive Resin Composition~

| | |
|---|---|
| Titanium dioxide dispersion liquid prepared above (dispersed composition) | 20.9 parts |
| Cyclomer P-ACA (solid content = 50% by mass, weight-average molecular weight = 30000, from Daicel Corporation) | 13.66 parts |
| TO-2349 (from Toagosei Co., Ltd., 7:3 mixture of Compound B below and dipentaerythritol hexaacrylate) | 10.25 parts |
| Polymerization initiator (Compound C below; from BASF, trade name: Irgacure OXE01) | 0.50 parts |
| Compound (1) below (ultraviolet absorber) | 1.03 parts |
| Solvent (propylene glycol monomethyl ether acetate; from Daicel Corporation, trade name: MMPGAC) | 69.82 parts |
| Surfactant (fluorine-containing surfactant; from DIC Corporation, trade name: Megafac F144) | 0.01 parts |
| Polymerization inhibitor (p-methoxyphenol; from Kanto Chemical Co., Inc., trade name: p-methoxyphenol) | 0.0051 parts |

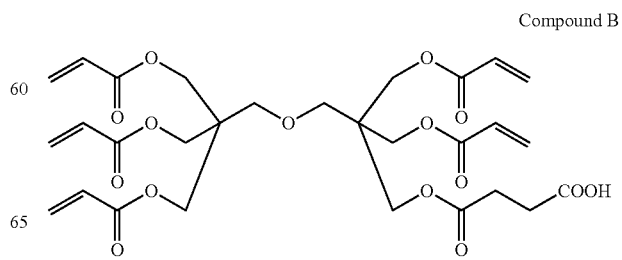

Compound B

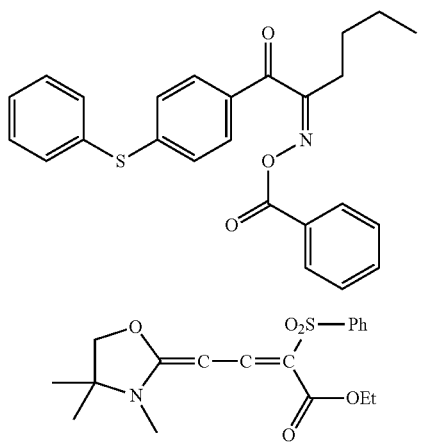

Compound C

Compound 1

<Formation of Coated Film>

The photo-sensitive resin composition obtained above was spin-coated over the planarizing film on the silicon wafer, and the work was heated for drying on a hot plate, at a surface temperature of the coated film of 100° C. for 120 seconds, to thereby form a coated film having a dry thickness of approximately 0.8 μm.

<Formation of Clear Pattern of Color Filter for Solid State Image Sensor>

Next, the dried coated film was exposed to light at a dose of 200 mJ/cm$^2$, using an i-line stepper (FPA-3000i5+, from Canon Inc.), through a mask pattern having 1.2-μm square pixels arrayed in every 4 mm×3 mm area on the substrate.

The coated film after the pattern-wise exposure was then subjected to puddle development using a 60% aqueous solution of an organic alkali developing solution CD-2000 (from FUJIFILM Electronic Materials Co., Ltd.) at room temperature for 60 seconds, and rinsed by spin showering for 20 seconds with pure water. Thereafter, the work was further rinsed with pure water. Water droplets were blown off with a high-pressure air, the substrate was allowed to dry naturally, and post-baked at 200° C. on a hot plate for 300 seconds, to form a clear pattern on the silicon wafer.

In this way, 1.2-μm square clear patterns were formed on the planarizing film on the silicon wafer, to thereby obtain a clear pattern of a color filter for solid state image sensor.

Next, according to conditions same as in the above-described manufacture of the clear pattern formed on the planarizing film on the silicon wafer, the photo-sensitive resin composition was coated over Corning Glass 1737 (from Corning Inc.) to form a coated film, and the coated film was then subjected to whole-surface exposure, development, rinsing, water washing and post-baking in this order so as to form a clear film of 1 μm thick, to thereby prepare a sample for measurement of transmittance.

<Evaluation>

The 1.2-μm square clear pattern, formed on the planarizing film on the silicon wafer as described above, was measured as described below. Evaluation and results of measurement were summarized in Table below.

(1) Transmittance

Transmittance at 400 nm of the obtained clear film was measured using a UV meter (UV-1800). The larger the transmittance at 400 nm, the better the translucency.

~Evaluation Criteria~

5: transmittance>85%

4: 85%≥transmittance>80%

3: 80%≥transmittance>70%

2: 70%≥transmittance>60%

1: 60%≥transmittance (2) Evaluation of Refractive Index

Refractive index of the obtained clear film was measured using an ellipsometer VUV-VASE (from J.A. Woollam Japan Corporation).

~Criteria for Determination~

3: 3.00>refractive index at 500 nm≥1.64

2: 1.64>refractive index at 500 nm≥1.50

1: refractive index at 500 nm<1.50

(3) Development Residue

The pixel pattern of the color filter after post-baking was observed under a critical dimension SEM (S-7800H, from Hitachi, Ltd.), from above the color filter on the silicon wafer at a 30000× magnification, and residence of the residue was visually evaluated according to the evaluation criteria below. The lesser the development residue, the better the pattern resolution.

~Evaluation Criteria~

3: Development residue not observed.

2: Slight development residue, but practically acceptable.

1: Considerable development residue.

Examples 2 to 9

Formation of Clear Pattern of Color Filter for Solid State Image Sensor

The photo-sensitive resin compositions were prepared, and the color filters were manufactured in the same way as in Example 1, except that species of the ultraviolet absorbers in the photo-sensitive resin compositions were altered as summarized in Table below. Evaluation was carried out in the same way as in Example 1. Evaluations and results of measurement were summarized in Table below.

Example 10

Formation of Clear Pattern of Color Filter for Solid State Image Sensor

The photo-sensitive resin composition was prepared, and the color filter was manufactured in the same way as in Example 2, except that species of the ultraviolet absorber in the photo-sensitive resin composition was altered as summarized in Table below, and the amount of consumption of the photo-polymerization initiator was changed to 2.5 parts. Evaluation was carried out in the same way as in Example 1. Evaluations and results of measurement were summarized in Table below.

Example 11

Formation of Clear Pattern of Color Filter for Solid State Image Sensor

The photo-sensitive resin composition was prepared and the color filter was manufactured in the same way as in Example 2, except that the photo-polymerization initiator was changed to 0.5 parts of Irgacure 369 (from BASF).

Evaluation was carried out in the same way as in Example 1. Evaluations and results of measurement were summarized in Table below.

Comparative Examples 1 to 3

Formation of Clear Pattern of Color Filter for Solid State Image Sensor

The photo-sensitive resin composition was prepared and the color filter was manufactured in the same way as in Example 1, except that species of the ultraviolet absorbers in the photo-sensitive resin compositions were altered as summarized in Table below. Evaluation was carried out in the same way as in Example 1. Evaluations and results of measurement were summarized in Table below.

TABLE 2

| No. | Ultraviolet absorber | Transmittance | Refractive index | Development residue |
|---|---|---|---|---|
| Example 1 | Compound 1 | 4 | 3 | 3 |
| Example 2 | Compound 2 | 5 | 3 | 3 |
| Example 3 | Compound 3 | 5 | 3 | 3 |
| Example 4 | Compound 4 | 4 | 3 | 3 |
| Example 5 | Compound 5 | 4 | 3 | 3 |
| Example 6 | Compound 6 | 4 | 3 | 3 |
| Example 7 | Compound 7 | 4 | 3 | 3 |
| Example 8 | Compound 8 | 4 | 3 | 3 |
| Example 9 | Compound 9 | 4 | 3 | 3 |
| Example 10 | Compound 2 | 4 | 3 | 2 |
| Example 11 | Compound 2 | 4 | 3 | 2 |
| Comparative Example 1 | Compound 29 | 3 | 3 | 3 |
| Comparative Example 2 | Compound 30 | 3 | 3 | 3 |
| Comparative Example 3 | — | 5 | 3 | 1 |

Note that Compounds 1 and so on in Table above correspond to the exemplary compounds summarized previously in Table 1 under the same numbering.

Compound 29 is ultraviolet absorber VIII-7 described in JP-A-2011-73214.

Compound 30 is ultraviolet absorber 47 described in JP-A-2009-96973.

As understood from Table above, the photo-sensitive resin compositions of this invention were found to show high refractive index, suppressed from being colored after the post-baking (having large transmittance), and, suppressed in development residue. It was also found that, further by using oxime compounds as the photo-polymerization initiator, and, by controlling the amount of mixing of the photo-polymerization initiator to 1 to 5% by mass relative to the photo-sensitive resin composition, the development residue was more effectively suppressed.

While Examples above explained the case where the clear pattern of color filter was formed on the silicon wafer, a solid state image sensor may be manufactured by replacing the silicon wafer, with a substrate for manufacturing solid state image sensor having photodiode, light shield film, device protective film and so forth formed thereon.

For example, a solid state image sensor (CCD, CMOS, etc.) featured by a good color reproducibility, may be manufactured by forming a light shielding film, made of tungsten and having openings only in the light receiving portions of the photodiodes, over a silicon wafer having diodes and transfer electrodes formed thereon; forming a device protective film made of silicon nitride, so as to cover the entire surface of the thus formed light shielding film and the light receiving portions of the photodiode (openings of the light shielding film); next by forming on the thus-formed device protective film, red pixels, blue pixels and green pixels according to a known method in the same way as in Examples described above, to thereby form the color filter; and then by forming microlenses as the light condensing means on the thus obtained color filter.

A film containing the ultraviolet absorber of this invention was manufactured, and was confirmed to show a good ultraviolet absorptivity.

What is claimed is:

1. A photo-sensitive resin composition comprising:
an ultraviolet absorber represented by Formula (III);
a photo-polymerization initiator; and
a polymerizable monomer:

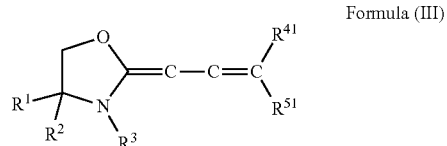

Formula (III)

wherein each of $R^1$, $R^2$ and $R^3$ independently represents a hydrogen atom or an alkyl group having 1 to 10 carbon atoms; and each of $R^{41}$ and $R^{51}$ independently represents a secondary or tertiary alkyl ester group.

2. The photo-sensitive resin composition of claim 1, which comprises the ultraviolet absorber represented by Formula (III) in an amount of 2 to 16% by mass, relative to the total solids content in the photo-sensitive resin composition.

3. The photo-sensitive resin composition of claim 1, wherein the ultraviolet absorber represented by Formula (III) has a molecular weight of 150 to 850.

4. The photo-sensitive resin composition of claim 1, wherein the ultraviolet absorber represented by Formula (III) is a compound represented by any of compounds (2) and (3) below:

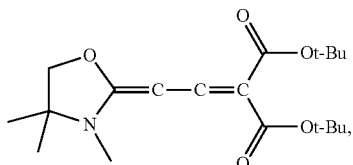

2

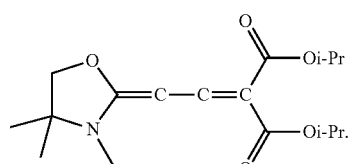

3

5. The photo-sensitive resin composition of claim 1, containing an oxime compound as the photo-polymerization initiator.

6. The photo-sensitive resin composition of claim 1, further comprising a particle having a refractive index at 500 nm of 1.80 to 2.80.

7. The photo-sensitive resin composition of claim 6, wherein the particle is composed of titanium dioxide and/or zirconium oxide.

8. The photo-sensitive resin composition of claim 1, further comprising a dye and/or a pigment.

9. The photo-sensitive resin composition of claim 1, further comprising an alkali-soluble resin.

10. The photo-sensitive resin composition of claim 1, intended to be used in formation of pixels of a solid state image sensor or a liquid crystal display device.

11. A cured film obtained by curing the photo-sensitive resin composition described in claim 1.

12. The cured film of claim 11, which comprises the ultraviolet absorber represented by Formula (III) in an amount of 0.01% by mass or less relative to the cured film.

13. A method for forming a pixel, the method comprising:
coating the photo-sensitive resin composition described in claim 1; and
photo-irradiating the thus-formed layer with at least ultraviolet radiation through a photomask, and then developing the layer to form a pattern; and
post-baking the thus formed pattern.

14. A color filter comprising the pixel formed by the method for forming a pixel described in claim 13.

15. A solid state image sensor comprising the color filter described in claim 14.

16. A liquid crystal display device comprising the color filter described in claim 14.

17. An ultraviolet absorber represented by Formula (III):

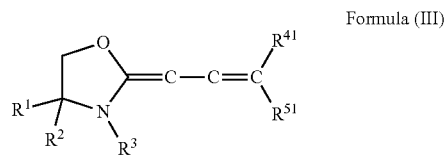

Formula (III)

wherein each of $R^1$, $R^2$ and $R^3$ independently represents a hydrogen atom or an alkyl group having 1 to 10 carbon atoms; and each of $R^{41}$ and $R^{51}$ independently represents a secondary or tertiary alkyl ester group.

* * * * *